United States Patent [19]

Higa et al.

[11] Patent Number: 4,962,216

[45] Date of Patent: Oct. 9, 1990

[54] PREPARATION OF DINEOPENTYLCADMIUM

[75] Inventors: Kelvin T. Higa; Daniel C. Harris, both of Ridgecrest, Calif.

[73] Assignee: The United States of America as represented by the Secretary of the Navy, Washington, D.C.

[21] Appl. No.: 417,222

[22] Filed: Sep. 29, 1989

Related U.S. Application Data

[63] Continuation of Ser. No. 164,311, Mar. 4, 1988, abandoned.

[51] Int. Cl.$^5$ ................................................ C07F 3/08
[52] U.S. Cl. ...................................... 556/129; 556/121
[58] Field of Search ........................ 556/129, 121, 118

[56] References Cited

U.S. PATENT DOCUMENTS

| | | |
|---|---|---|
| 2,082,568 | 6/1937 | Carothers .............................. 556/129 |
| 3,475,475 | 10/1969 | Eiot .................................. 556/121 X |
| 3,880,743 | 4/1975 | Lang ..................................... 556/70 |

OTHER PUBLICATIONS

Biochemistry, vol. 24, "Thermotropic Phase Behavior of Model Membranes Composed of Phosphatidylcholines Containing Iso-Branched Fatty Acids 1. Differential Scanning Calorimetic Studies", Lewis and McElhaney, pp. 2431-2439, 1985.

*Primary Examiner*—Arthur C. Prescott
*Attorney, Agent, or Firm*—Sol Sheinbein; Melvin J. Sliwka; Donald E. Lincoln

[57] ABSTRACT

Dineopentylcadmium is prepared from cadmium dihalide and neopentyl Grignard in tetrahydrofuran. The reaction product is isolated by addition of dioxane, filtration, removal of solvent via distillation, and purification by sublimation.

26 Claims, No Drawings

PREPARATION OF DINEOPENTYLCADMIUM

CROSS-REFERENCE TO RELATED APPLICATION

This application is a continuation of earlier filed copending application Ser. No. 07/164,311 now abandoned, entitled Preparation of Dineopentylcadmium, filed on Mar. 4, 1988, by Kelvin T. Higa and Daniel C. Harris which is hereby incorporated by reference for the purpose of claiming the benefit of the earlier filing date.

BACKGROUND OF THE INVENTION

1. Field of the Invention

The present invention is related to metal-organic compounds. More particularly, the invention is related to cadmium and a method for synthesis of the new compound dineopentylcadmium.

2. Description of the Invention

Metal-Organic Chemical Vapor Deposition film growth of Mercury-Cadmium-Telluride ($Hg_{1-x}Cd_xTe$) is adversely affected by premature upstream reaction of the dialkyltelluride and the dialkylcadmium source compounds, which result in poor film morphology and a high number of site defects. With the use of diorganocadmium compounds with sterically bulky alkyl groups, the premature reaction may be reduced and film quality improved.

SUMMARY OF THE INVENTION

A new dialkylcadmium compound has been synthesized and found to be useful as a cadmium source compound in the metal-organic chemical vapor deposition of mercury-cadmium-telluride. The new dialkylcadmium compound is prepared from the reaction between cadmium dihalide and 2 equivalents of an neopentyl magnesium chloride in tetrahydrofuran. Dioxane is added, the mixture filtered, the solvent removed by distillation and the final product isolated by sublimation.

DETAILED DESCRIPTION OF THE INVENTION

According to the present invention, the composition of matter, dineopentylcadmium, is prepared in an efficient process.

The new compound, dineopentylcadmium, offers many advantages over dimethylcadmium as a cadmium source compound for the metal-organic chemical vapor deposition of mercury-cadmium-telluride. For example, premature upstream reaction is significantly reduced as demonstrated by a much cleaner reactor after cadmium-telluride (CdTe) film deposition and a better CdTe film morphology than previously possible.

Dineopentylcadmium is prepared, under inert atmosphere, by a process in which cadmium dichloride and two equivalents of neopentyl magnesium chloride are combined in tetrahydrofuran at $-78°$ C. to $25°$ C., then heated to $68°$ C. for 4 hours in the absence of light by wrapping the apparatus in aluminum foil or covering it with a dark cloth. Dioxane is added, the mixture of solid and liquid fractions separated by filtration, the solvent removed via distillation, and the product isolated via sublimation. Dineopentylcadmium is produced in yields as high as 84%.

Dineopentylcadmium can be prepared by the reaction of cadmium dihalide with at least two equivalents of neopentyl magnesium halide in a solvent, where halide may be chloride, bromide or iodide. Solvents which may be used include tetrahydrofuran, pentane, hexane, heptane, benzene, toluene, xylene, and diethyl ether. The inert atmosphere can be the inert gases argon, nitrogen or helium.

EXAMPLE

All manipulations were performed using standard Schlenk techniques, in an inert atmosphere, and in the absence of light, by wrapping in aluminum foil and covering with a dark cloth, unless otherwise noted.

A 200 mL Schlenk flask was charged with 5.64 g (232 mmol) of magnesium turnings and equipped with a magnetic stir bar and a rubber septum in a glove box. About 150 mL of tetrahydrofuran was added via cannula, then 24.3 g (228 mmol) of neopentyl chloride and a crystal of iodine were added. The septum was replaced by a water condenser and the reaction mixture was refluxed for 4 hours with stirring, and then allowed to cool to room temperature. The reflux condenser was replaced with a solids addition funnel containing 16.4 g (89.4 mmol) of cadmium dichloride ($CdCl_2$). The entire apparatus was under inert atmosphere, wrapped with aluminum foil and covered with a black cloth. The cadmium dichloride was added over a period of 20 minutes at $-78°$ C. to $25°$ C. The reaction mixture was refluxed for 4 hours at $68°$ C., 50 mL of dioxane added and the reaction mixture filtered. Fresh tetrahydrofuran was added to the solid on the frit and the mixture filtered. The tetrahydrofuran was removed from the combined filtrate via distillation under inert atmosphere to give an off-white solid as the crude product. The crude product was sublimed at $25°$ C. at $10^{-2}$ torr onto a $-78°$ C. cold finger.

A total of 19.1 g (75.1 mmol, 84%) of dineopentylcadmium was obtained as a crystalline white, air sensitive, light-stable solid. Melting point $42°$ C. Mass spectrum (parent): 254($^{112}$Cd), 256 ($^{114}$Cd).

The $^1H$ nuclear magnetic resonance spectrum in deuterobenzene exhibits singlets at 1.04 and 0.64 ppm. The $^{113}Cd$ nuclear magnetic resonance spectrum of a 1 molar solution of the product in deuterobenzene exhibits a singlet at $-30.7$ ppm as referenced to a 0.1 molar $Cd(NO_3)_2$ in $D_2O$, whose chemical shift was set at $-644.7$ ppm.

Modification and variation of the present invention are possible. It should be understood that, within the scope of the appended claims, the invention may be practiced otherwise than as specifically described.

What is claimed is:

1. A method for preparing dineopentylcadmium, comprising the steps of:
   (a) adding cadmium dihalide to at least two equivalents of neopentyl magnesium halide in a solvent under inert atmosphere and darkened conditions;
   (b) refluxing the reaction mixture;
   (c) adding dioxane to the reaction mixture;
   (d) filtering the reaction mixture to obtain a solid fraction and a liquid fraction thereof containing the product;
   (e) distilling said liquid fraction under inert atmosphere to remove said solvent, leaving a crude product; and
   (f) subliming the crude product to yield dineopentylcadmium.

2. The method of claim 1 wherein said halides are selected from the group consisting of chloride, bromide or iodide.

3. The method of claim 1 wherein said solvent is selected from the group consisting of tetrahydrofuran, pentane, hexane, heptane, benzene, toluene, xylene and diethyl ether.

4. The method of claim 1 wherein said inert atmosphere is selected from the group of inert gases consisting of argon, nitrogen and helium.

5. A method for preparing dineopentylcadmium, comprising the steps of:
   (a) adding cadmium dihalide to at least two equivalents of neopentyl magnesium halide in a solvent under inert atmosphere and darkened conditions;
   (b) refluxing the reaction mixture;
   (c) adding at least two equivalents of dioxane to the reaction mixture;
   (d) filtering the reaction mixture to obtain a solid fraction and a liquid fraction;
   (e) distilling said liquid fraction under inert atmosphere to remove said solvent, leaving a crude product; and
   (f) subliming the crude product to yield dineopentylcadmium.

6. The method of claim 5 wherein said halides are selected from the group consisting of chloride, bromide and iodide.

7. The method of claim 5 wherein said solvents are selected from the group consisting of tetrahydrofuran, pentane, hexane, heptane, benzene, toluene, xylene and diethyl ether.

8. The method of claim 5 wherein said inert atmosphere is selected from the group of inert gases consisting of argon, nitrogen and helium.

9. A method for preparing dineopentylcadmium, comprising the steps of:
   (a) adding, over a period of time, cadmium dihalide to at least two equivalents of neopentyl magnesium halide in a solvent under inert atmosphere and darkened conditions at a temperature from about $-78°$ C. to about 25° C.;
   (b) refluxing the reaction mixture for about 4 hours;
   (c) adding at least two equivalents of dioxane to the reaction mixture;
   (d) filtering the reaction mixture to obtain a solid fraction and a liquid fraction containing the crude product therein;
   (e) distilling said liquid fraction under inert atmosphere to remove said solvent, leaving a crude product; and
   (f) subliming the crude product to yield dineopentylcadmium.

10. The method of claim 9 wherein said period of time to add said neopentyl metal halide to said cadmium dihalide is about 20 minutes.

11. The method of claim 9 wherein said halides are selected from the group consisting of chloride, bromide and iodide.

12. The method of claim 9 wherein said solvents are selected from the group consisting of tetrahydrofuran, pentane, hexane, heptane, benzene, toluene, xylene and diethyl ether.

13. The method of claim 9 wherein said inert atmosphere is selected from the group of inert gases consisting of argon, nitrogen and helium.

14. The method of claim 9 wherein said subliming of crude produce is at about 25° C. at about $10^{-2}$ torr onto a cold finger at about $-78°$ C.

15. A method for preparing dineopentylcadmium, comprising the steps of:
   (a) adding cadmium dihalide to at least two equivalents of neopentyl magnesium halide in a solvent under inert atmosphere and darkened conditions over a period of about 20 minutes at about $-78°$ C. to about 25° C.;
   (b) refluxing the reaction mixture at about 68° C. for about 4 hours;
   (c) adding at least two equivalents of dioxane to the reaction mixture;
   (d) filtering the reaction mixture to obtain a solid fraction and a liquid fraction thereof containing the product;
   (e) distilling said liquid fraction under inert atmosphere to remove said solvent, leaving a crude product; and
   (f) subliming the crude product to yield dineopentylcadmium.

16. The method of claim 15 wherein said halides are selected from the group consisting of chloride, bromide and iodide.

17. The method of claim 15 wherein said solvents are selected from the group consisting of tetrahydrofuran, pentane, hexane, heptane, benzene, toluene, xylene and diethyl ether.

18. The method of claim 15 wherein said inert atmosphere is selected from the group of inert gases consisting of argon, nitrogen and helium.

19. The method of claim 15 wherein subliming of crude product is at about 25° C. at about $10^{-2}$ torr onto a cold finger at about $-78°$ C.

20. A method for preparing dineopentylcadmium, comprising the steps of:
   (a) adding, over a 20 minute time period, cadmium dihalide to at least two equivalents of neopentyl magnesium halide in a solvent under inert atmosphere and darkened conditions at about $-78°$ C. to about 25° C.;
   (b) refluxing the reaction mixture at about 68° C., for about 4 hours;
   (c) adding at least two equivalents of dioxane to the reaction mixture;
   (d) filtering the reaction mixture to obtain a solid fraction and a liquid fraction containing the product;
   (e) adding more of said solvent to said solid fraction;
   (f) filtering the mixture again;
   (g) distilling said liquid fraction under inert atmosphere to remove said solvent, leaving a crude product; and
   (h) subliming the crude product to yield dineopentylcadmium.

21. The method of claim 20 wherein said halides are selected from the group consisting of chloride, bromide and iodide.

22. The method of claim 20 wherein said solvents are selected from the group consisting of tetrahydrofuran, pentane, hexane, heptane, benzene, toluene, xylene and diethyl ether.

23. The method of claim 20 wherein said inert atmosphere is selected from the group of inert gases consisting of argon, nitrogen and helium.

24. The method of claim 20 wherein said subliming crude product is at about 25° C. at about $10^{-2}$ torr onto a cold finger at about −78° C.

25. A method for preparing dineopentylcadmium, comprising the steps of:
(a) adding cadmium dichloride to at least two equivalents of neopentyl magnesium chloride in tetrahydrofuran over a 20 minute time period under nitrogen and darkened conditions at about −78° C. to about 25° C.;
(b) refluxing the reaction mixture at about 68° C. for about 4 hours;
(c) adding at least two equivalents of dioxane to the reaction mixture;
(d) filtering the reaction mixture to obtain a solid fraction and a liquid fraction containing the crude product therein;
(e) adding more tetrahydrofuran to said solid fraction;
(f) filtering the mixture again;
(g) distilling said liquid fraction under nitrogen to remove said tetrahydrofuran, leaving a crude product; and
(h) subliming the crude product at about 25° C. at about $10^{-2}$ torr onto a cold finger at about −78° C. to yield dineopentylcadmium.

26. A compound, dineopentylcadmium.

* * * * *